United States Patent [19]

Syrier et al.

[11] 4,281,203
[45] Jul. 28, 1981

[54] (CYCLOPROPYL)VINYL ALKYL ETHER DERIVATIVES

[75] Inventors: Johannes L. M. Syrier; Johannes Van Berkel, both of Amsterdam, Netherlands

[73] Assignee: Shell Oil Company, Houston, Tex.

[21] Appl. No.: 153,996

[22] Filed: May 28, 1980

[30] Foreign Application Priority Data

Jun. 1, 1979 [GB] United Kingdom ............... 19266/79

[51] Int. Cl.$^3$ ..................... C07C 49/21; C07C 43/162
[52] U.S. Cl. ................................. 568/303; 568/669;
568/591; 568/420; 560/231; 562/506;
260/343.3 R; 260/343.21
[58] Field of Search ............... 568/669, 361, 303, 591,
568/691

[56] References Cited

U.S. PATENT DOCUMENTS

| | | | |
|---|---|---|---|
| 3,021,373 | 2/1962 | Montagna et al. | 568/691 |
| 3,819,677 | 6/1974 | Gale | 568/591 X |
| 4,045,422 | 8/1977 | Rogic et al. | 568/361 X |
| 4,222,964 | 9/1980 | Van Berkel et al. | 568/591 X |

OTHER PUBLICATIONS

Methoden der Organischen Chemie, (Houben-Weyl), vol. VI/3, (1965), pp. 97–102.

Primary Examiner—Bernard Helfin

[57] ABSTRACT

New compounds of formula:

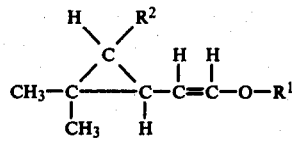

wherein $R^1$ is an alkyl group and $R^2$ a 2-oxopropyl group or a 2,2-dihalovinyl group are prepared by elimination of an alcohol $R^1OH$ from an acetal of formula:

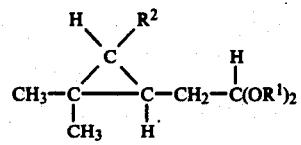

The compounds are intermediates in route to pyrethroid insecticides.

4 Claims, No Drawings

(CYCLOPROPYL)VINYL ALKYL ETHER DERIVATIVES

BACKGROUND OF THE INVENTION

1. Field of the Invention

The present invention is directed to new (cyclopropyl)vinyl alkyl ether derivatives and to a process for the preparation of these derivatives.

2. Description of the Prior Art

The cyclopropanecarboxylate esters are insecticidally-active compounds known as "pyrethroids" and as they combine exceptionally good insecticidal properties with a very low mammalian toxicity, they are of great interest to the agrochemical industry. Therefore, considerable effort has been expended in finding economic routes to them and to their principal intermediates.

The general formula of one class of these pyrethroids may be represented as follows:

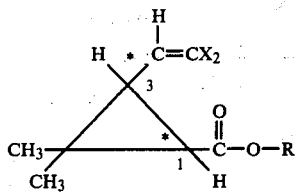

wherein each asterisk denotes a chiral carbon atom; each X is a halogen atom and R is a member of a group of radicals known to impart insecticidal activity to the molecule, e.g. 3-phenoxybenzyl or alpha-cyano-3-phenoxybenzyl. It is known that for maximum insecticidal activity the stereoisomeric form of the acid part of the ester of the above-mentioned formula should be 1R,cis, i.e. the absolute configuration at carbon atom 1 is R and the two hydrogen atoms on carbon atoms 1 and 3 are in a cis relationship. This nomenclature is known as the Elliott nomenclature and is defined in M. Elliott c.s., Nature, 1974, 248, 710.

It follows, therefore, that if 1R,cis esters of the above-mentioned formula are to be prepared, either a stereospecific chemical route is required or the desired stereoisomer must be obtained from a racemic mixture by physical separation techniques. The latter techniques are expensive and laborious and not readily employed on an industrial scale. The Applicant has found two stereo-specific routes which use as starting material the naturally-occurring substance (+)-3-carene whose formula is as follows:

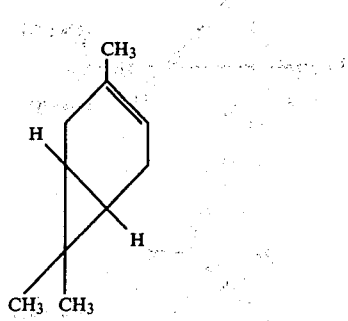

This compound is an inexpensive, readily available natural terpene. The present application discloses two routes to the (1R,cis)-acid portion of the pyrethroid ester mentioned hereinbefore, starting from (+)-3-carene and proceeding via novel cyclopropane compounds according to the invention.

SUMMARY OF THE INVENTION

The present invention provides compounds of the general formula:

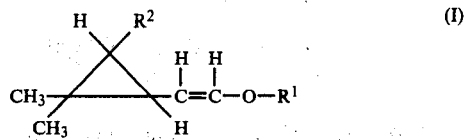

wherein $R^1$ represents an alkyl group and $R^2$ a 2-oxopropyl group or a 2,2-dihalovinyl group.

$R^1$ in the general formula I preferably represents an alkyl group with fewer than six carbon atoms, for example, a methyl, ethyl, n-propyl or isopropyl group. Most preferably $R^1$ represents a methyl group. The two halogen atoms in the 2,2-dihalovinyl group, i.e. fluorine, chlorine, bromine or iodine atoms, may be the same or different and are preferably chlorine or bromine atoms.

Particularly preferred compounds of formula I are: 2-[2-(2,2-dichlorovinyl)-3,3-dimethylcyclopropyl]vinyl methyl ether, hereinafter also referred to as "compound A" and having the structural formula:

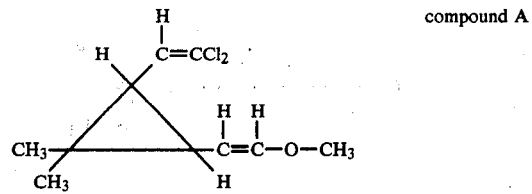

and 2-[2,2-dimethyl-3-(2-oxopropyl)cyclopropyl]vinyl methyl ether, hereinafter also referred to as "compound B" and having the structural formula:

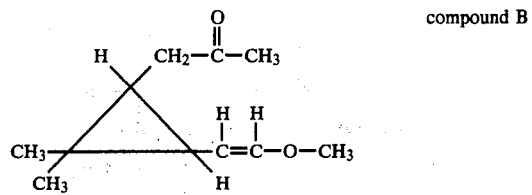

As the compounds of the general formula I have two chiral carbon atoms and a vinyl group with unequal substituents at each of the carbon atoms, they have a number of isomers; these compounds may exist in any of these isomers or mixtures thereof. As they are intermediates in the preparation of pyrethroids, compounds A and B are preferably in the (1R,cis) form, 1 denoting the underlined carbon atom in the group H—C—C(H)=C in compounds A and B; compounds A and B may have the cis or the trans form with respect to the carbon carbon double bond or may consist of mixtures of these cis and trans isomers.

The compounds and their preferred stereoisomeric form according to the invention may be prepared by processes known per se, preferably by elimination of alcohols from acetals as described in "Methoden der organischen Chemie," Volume VI/3 (1965) 97-102. Accordingly, the invention provides a process for the preparation of compounds of formula I, characterized in that an alkanol of the general formula $R^1OH$, wherein $R^1$ has the same meaning as in formula I, is eliminated from an acetal of the general formula:

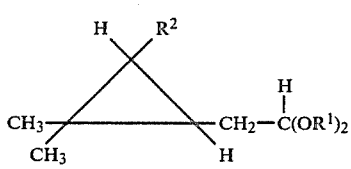
(II)

wherein $R^1$ and $R^2$ have the same meaning as in the general formula I.

$R^1$ in the general formula II preferably represents an alkyl group with fewer than six carbon atoms, for example, a methyl, ethyl or propyl group. $R^1$ most preferably represents a methyl group. The two halogen atoms in the 2,2-dihalovinyl group, i.e. fluorine, chlorine, bromine or iodine atoms, may be the same or different and are preferably chlorine or bromine atoms. Preferred starting compounds of the general formula II are 2-[2-(2,2-dichlorovinyl)-3,3-dimethylcyclopropyl]acetaldehyde dimethyl acetal having the structural formula:

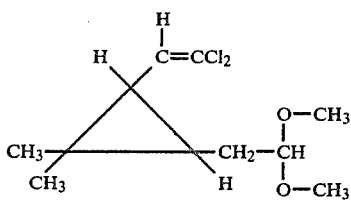

and
2-[2,2-dimethyl-3-(2-oxopropyl)cyclopropyl]acetaldehyde dimethyl acetal having the structural formula:

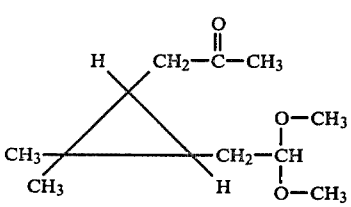

Very high selectivities to the compounds of formula I at very high conversions of the starting acetal of formula II have been obtained by reacting this acetal with phosphorus oxychloride in the presence of pyridine. The selectivity to a certain compound, expressed in a percentage, is defined as $a/b \times 100$ wherein "a" is the amount of the starting compound converted into that certain compound and "b" is the amount of converted starting compound.

In the above-mentioned process phosphorus oxychloride may be replaced by diphosphorus pentaoxide, and pyridine by quinoline. If desired, a solvent for the organic compounds in question may be used, for example an aromatic hydrocarbon such as toluene or one or more xylenes.

The compounds according to the invention are of interest in a multi-step route to pyrethroid insecticides. An example of such a multi-step route is schematically given below:

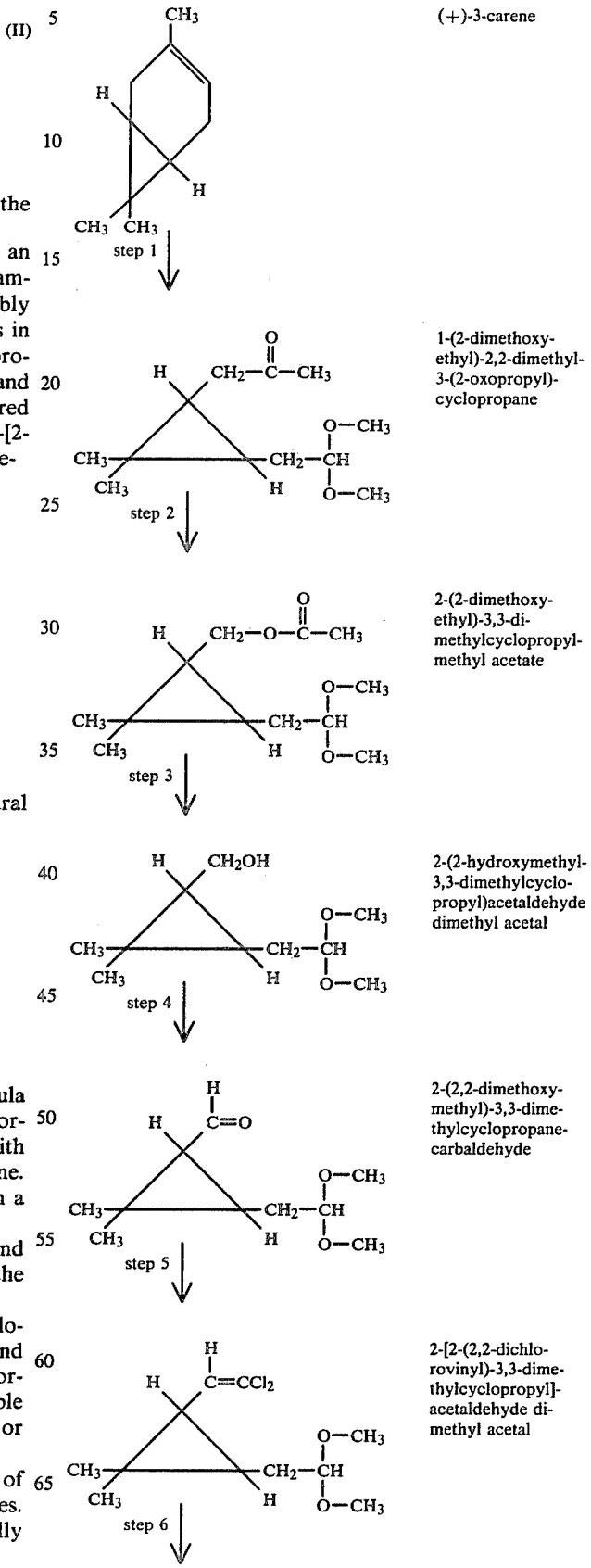

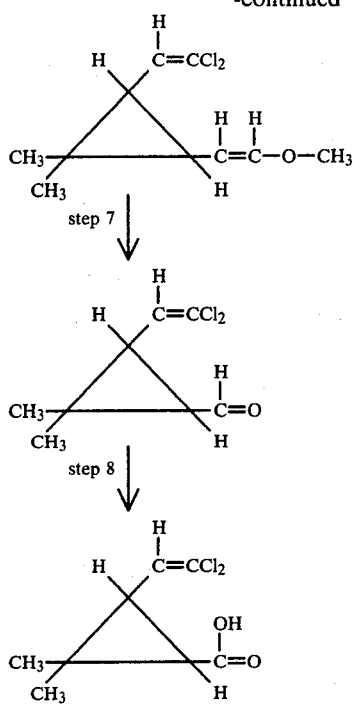

Details of this multi-step process are given below.

Step 1

Ozonolysis of (+)-3-carene, followed by reduction of the ozonolysis product formed (for example, with dimethyl sulphide, triethyl amine or zinc dust and acetic acid) in the presence of methanol and an acetalizing catalyst (for example, p-toluenesulphonic acid) yields a stereoisomer of 1-(2,2-dimethoxyethyl)-2,2-dimethyl-3-(2-oxopropyl)-cyclopropane. Ozonolysis of organic compounds and reduction of the peroxidic ozonolysis products is described in, for example, Chemical Reviews 58 (1958) 925–995.

Step 2

Oxidation of the cyclopropane derivative obtained in step 1 with a peroxy acid in the presence of a solvent yields a stereoisomer of 2-(2,2-dimethoxyethyl)-3,3-dimethylcyclopropylmethyl acetate, as described in European patent 2,850 and its counterpart, allowed U.S. application Ser. No. 966,681, filed Dec. 5, 1978, now U.S. Pat. No. 4,230,891. Oxidation of ketones to esters is described in "Methoden der organischen Chemie," Volume VIII (1952) 559–560. Examples of peroxy acids are perbenzoic acid, 3-chloroperbenzoic acid and peracetic acid.

Step 3

Hydrolysis of the ester obtained in step 2 yields a stereoisomer of 2-(2-hydroxymethyl-3,3-dimethylcyclopropyl)acetaldehyde dimethyl acetal, as described in British patent publication No. 2,025,965 and U.S. application Ser. No. 59,854, now U.S. Pat. No. 4,241,081, filed July 23, 1979, as a continuation-in-part of U.S. application Ser. No. 953,987, filed Oct. 23, 1978, now abandoned. Hydrolysis of esters is described in "Methoden der organischen Chemie," Volume VIII (1952) 418–423 and 638–639. The hydrolysis is carried out in such a manner that the two methoxy groups remain unchanged; this may be achieved by using an alkaline-reacting medium.

Step 4

Oxidation of the alcohol obtained in step 3 yields a stereoisomer of 2-(2,2-dimethoxyethyl)-3,3-dimethylcyclopropanecarbaldehyde, as described in British patent publication No. 2,025,964 and its U.S. counterpart, allowed U.S. Ser. No. 55,857, filed July 9, 1979, now U.S. Pat. No. 4,234,512. This oxidation of primary alcohols to aldehydes is described in, for example, "Methoden der organischen Chemie," Volume VII, Part I (1954) 159–192. The oxidation is suitably carried out with the chromium trioxide-pyridine complex, as described in J. Org. Chem. 35 (1970) No. 11, 4000–4002.

Step 5

Reaction of a tri(dialkylamino)phosphine or an alkyl ester of an ortho-phosphorus acid bis(dialkylamide) with a tetrahalomethane or a trihalomethane and reaction of the product thus obtained with the aldehyde obtained in step 4 yields 2-[2-(2,2-dichlorovinyl)-3,3-dimethylcyclopropyl]acetaldehyde dimethyl acetal, as described in British patent application 30340/78 and its allowed U.S. counterpart, allowed U.S. Ser. No. 55,857, filed July 9, 1979, now U.S. Pat. No. 4,234,512.

Step 6

Elimination of methanol, for example, in the manner described hereinbefore, from the acetal obtained in step 5 yields a stereoisomer of compound A.

Step 7

Oxidation of compound A yields a stereoisomer of 2-(2,2-dichlorovinyl)-3,3-dimethylcyclopropanecarbaldehyde. This oxidation may be carried out with, for example:

(a) ozone, followed by reduction of the ozonolysis product formed, or (b) hydrogen peroxide in the presence of molybdenum trioxide, or (c) a peroxy acid (for example, peracetic acid) in the presence of a compound neutralizing the acid simultaneously formed (for example, sodium carbonate or sodium hydrogen carbonate), water and a water-immiscible organic solvent (for example, 1,2-dichloroethane).

Step 8

Oxidation of the aldehyde formed in step 7 with, for example, hydrogen peroxide in alkaline medium, yields a stereoisomer of 2-(2,2-dichlorovinyl)-3,3-dimethylcyclopropanecarboxylic acid, whose structure was found to be the same as that of the (1R,cis)-form of the acid. Esters of this acid are very active insecticidal compounds, as described in U.S. Pat. No. 4,024,163.

Another example of a multi-step route to pyrethroids is schematically given below:

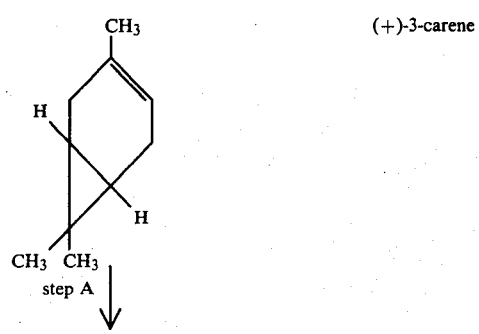

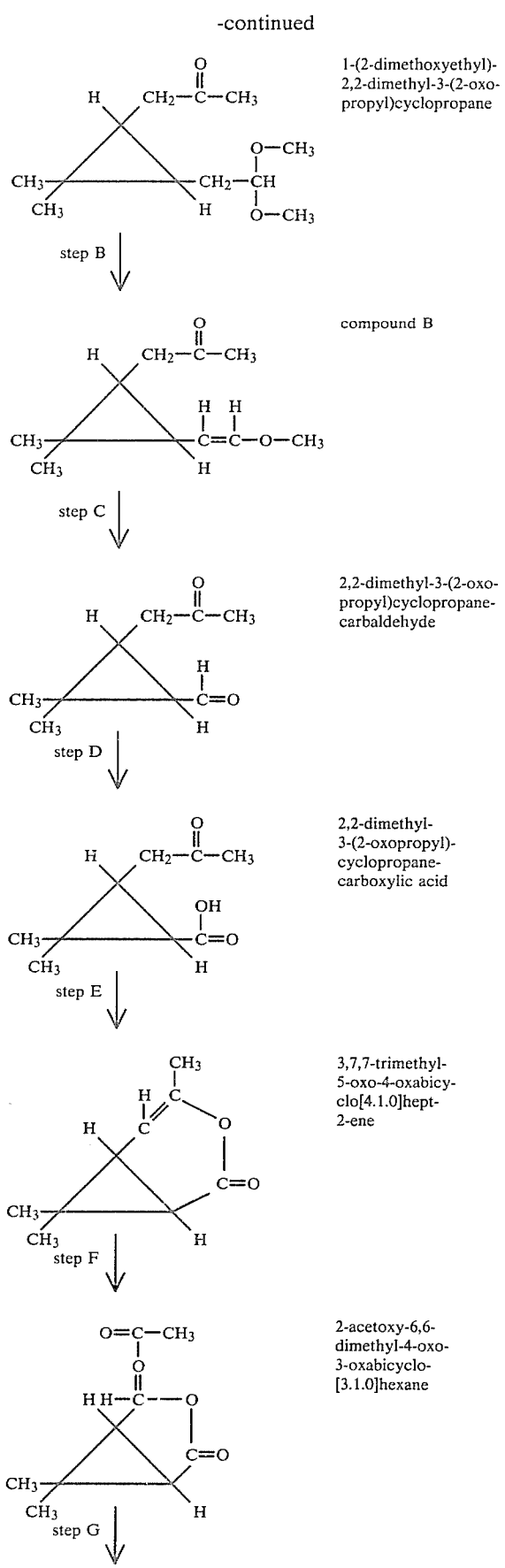
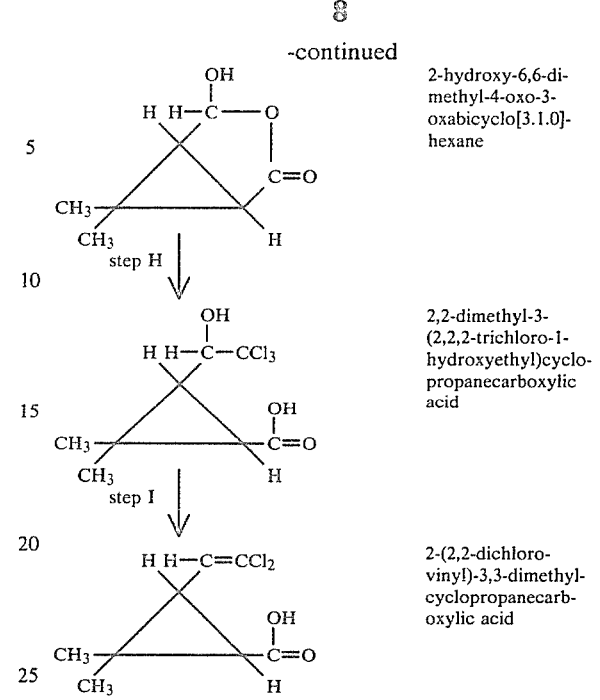

Details of the latter multi-step route are given below:

Step A

This step is the same as step 1 described hereinbefore.

Step B

Elimination of methanol, for example, in the manner described hereinbefore, from the acetal obtained in step A, yields a stereoisomer of compound B.

Step C

Ozonolysis of compound B, followed by reduction of the ozonolysis product formed (for example, with dimethyl sulphide) yields a stereoisomer of 2,2-dimethyl-3-(2-oxopropyl)cyclopropanecarbaldehyde as described hereinafter in Example III.

Step D

Oxidation of the aldehyde formed in step C with, for example, hydrogen peroxide in alkaline medium, or with potassium permanganate, yields a stereoisomer of 2,2-dimethyl-3-(2-oxopropyl)cyclopropane-carboxylic acid. Oxidation of aldehydes to carboxylic acids is described in "Methoden der organischen Chemie," Volume VIII (1952) 407–413.

Step E

Dehydration of the acid obtained in step D, for example, with acetic anhydride in the presence of p-toluenesulphonic acid and a solvent, yields a stereoisomer of 3,7,7-trimethyl-5-oxo-4-oxabicyclo[4.1.0]hept-2-ene, as described in U.S. Pat. No. 4,132,717.

Step F

Epoxidation of the bicyclic compound obtained in step E using standard epoxidation reactions yields 2,3-epoxy-3,7,7-trimethyl-5-oxo-4-oxabicyclo[4.1.0]heptane, isomerization of this epoxy compound yields 2-acetyl-6,6-dimethyl-4-oxo-3-oxabicyclo[3.1.0]hexane, and oxidation of the latter compound yields 2-acetoxy-6,6-dimethyl-4-oxo-3-oxabicyclo[3.1.0]hexane. This sequence of reactions may be carried out with the aid of a peroxy acid in one single step, as described in British patent application 7,912,133 and its pending U.S. counterpart application Ser. No. 135,405, filed March 31, 1980 and now U.S. Pat. No. 4,257,956.

Step G

Saponification of the acetoxy compound obtained in step F, for example, in the presence of a water-containing organic solvent and an alkali metal hydroxide and acidification of the reaction mixture thus obtained yields 2-hydroxy-6,6-dimethyl-4-oxo-3-oxabicyclo[3.1.0]hexane.

Step H

This step may be carried out as described in Bull. of Acad. of Sci., USSR, 11, 2426-3, (1975) or in British patent application 7,910,661 and its pending U.S. counterpart application Serial No. 133,773, filed Mar. 25, 1980, by reaction of the bicyclic compound obtained in step G with an alkali metal trihaloacetate in a highly polar, aprotic, inert solvent, followed by acidification of the reaction mixture, thus forming 2,2-dimethyl-3-(2,2,2-trichloro-1-hydroxyethyl)-cyclopropanecarboxylic acid.

Step I

This step may be carried out as described in Netherlands patent application 7806915 and Belgian patent 868,445 by heating the acid obtained in step H, or by reaction of this acid with an acidic reactant or a dehydrating agent, to form the lactone of this acid, which lactone in turn is reacted with a reducing agent (for example, zinc in the presence of acetic acid) with formation of 2-(2,2-dichlorovinyl)-3,3-dimethylcyclopropanecarboxylic acid.

The following Examples further illustrate the invention. The conversions, selectivities and purities were determined by means of gas-liquid chromatography and nuclear magnetic resonance (NMR) spectroscopy. The NMR data quoted were recorded at 90 MHz using solutions of the compounds in deuterochloroform and tetramethylsilane as an internal standard.

EXAMPLE I—Preparation of 1R,cis compound A.

The contents of a 50-ml flask charged with 1R,cis 2-[2-(2,2-dichlorovinyl)-3,3-dimethylcyclopropyl]acetaldehyde dimethyl acetal (10.3 mmol), phosphorus oxychloride (10.4 mmol), pyridine (55.4 mmol, 4.3 ml) and toluene (13 ml) were stirred for 4.5 hours at a temperature between 90° and 95° C. At the end of this period the selectivity to 1R,cis compound A was more than 90% at 95% conversion of the starting acetal. The cis/trans ratio with respect to the two underlined hydrogen atoms in the group —$\underline{H}$C=C($\underline{H}$)—OCH$_3$ was 2:1.

The mixture in the flask was allowed to adopt a temperature of 20° C., a 10 %w aqueous solution (20 ml) of sodium chloride was added, the mixture obtained was allowed to separate into an aqueous and a toluene phase, the aqueous phase was washed twice with toluene (20 ml) and the combined three toluene phases were washed with a 10 %w aqueous solution (30 ml) of sodium chloride, the washed toluene phase was dried over anhydrous magnesium sulphate and the dried liquid was subjected to distillation at sub-atmospheric pressure to leave a residue (1.7 g) containing 1R,cis compound A in a yield of 75%.

The NMR spectrum of 1R,cis compound A showed the following absorptions in deuterochloroform:

$\delta$=1.03 ppm, singlet, C$\underline{H}_3$—C—CH$_3$
$\delta$=1.19 ppm, singlet, CH$_3$—C—C$\underline{H}_3$
$\delta$=5.60 ppm, doublet, $\underline{H}$C=CCl$_2$, J=9 Hz
$\delta$=6.07 ppm, double doublet, cis HC=C($\underline{H}$)—OCH$_3$, $J_1$=6 Hz; $J_2$=1 Hz
$\delta$=6.39 ppm, doublet, trans HC=C($\underline{H}$)—OCH$_3$, J=13 Hz
$\delta$=4.10 ppm, double doublet, cis $\underline{H}$C=C(H)—O—CH$_3$, $J_1$=6 Hz, $J_2$=7 Hz
$\delta$=4.5 ppm, double doublet, trans $\underline{H}$C=C(H)—O—CH$_3$
$\delta$=3.65 ppm, singlet, cis-O—C$\underline{H}_3$
$\delta$=3.55 ppm, singlet, trans—O-CH$_3$ multiplets for C=C—C($\underline{H}$)—C($\underline{H}$)—C=C EXAMPLE II—Preparation of 1R,cis compound B The contents of a 250-ml flask charged with 1R,cis 2-[2,2-dimethyl-3-(2-oxopropyl)cyclopropyl]acetaldehyde dimethyl acetal (98.1 mmol), phosphorus oxychloride (103.3 mmol), pyridine (521 mmol, 42 ml) and toluene (100 ml) were stirred for 2 hours at 85° C. At the end of this period the selectivity to 1R,cis compound B was 88% at 96% conversion of the starting acetal. The cis/trans ratio with respect to the two underlined hydrogen atoms in the group —($\underline{H}$)C=C($\underline{H}$)—O—CH$_3$ was 3:2.

1R,cis compound B was isolated from the reaction mixture in the manner described for 1R,cis compound A in example I. The yield of 1R,cis compound B was 72%.

The NMR spectrum of 1R,cis compound B showed the following absorptions in deuterochloroform:

$\delta$=0.93 ppm, singlet, cis+trans C$\underline{H}_3$—C—CH$_3$
$\beta$=1.12 ppm, singlet, trans CH$_3$—C—CH$_3$
$\delta$=1.14 ppm, singlet, cis CH$_3$—C—CH$_3$
$\delta$=2.2–2.4 ppm, one doublet for cis and one doublet for trans, C$\underline{H}_2$—C=O
$\delta$=2.17 ppm, singlet, C$\underline{H}_3$—C=O
$\delta$=4.00 ppm, double doublet, cis $\underline{H}$C=C(H)—OCH$_3$, $J_1$=9 Hz, $J_2$=6 Hz
$\delta$=4.40 ppm, double doublet, trans $\underline{H}$C=C(H)—OCH$_3$, $J_1$=13 Hz, $J_2$=8 Hz
$\delta$=6.03 ppm, double doublet, cis HC=C($\underline{H}$)—OCH$_3$, $J_1$=6 Hz, $J_2$=1 Hz
$\delta$=6.34 ppm, doublet, trans HC=C($\underline{H}$)—OCH$_3$, J=13 Hz.
$\delta$=3.60 ppm, singlet, cis —O—C$\underline{H}_3$
$\delta$=3.52 ppm, singlet, trans—O-CH$_3$ multiplets for O=C—CH$_2$—C($\underline{H}$)—C=C

EXAMPLE III

A stream of ozone in air was bubbled into the contents of a 50-ml flask kept at a temperature of −78° C. and charged with 1R,cis compound B (prepared as described in Example II, purity 70%, 1.73 mmol) and dichloromethane (20 ml) until a faint blue colour persisted. The solution was purged with air to remove excess ozone and a solution of dimethyl sulphide (3 mmol) in dichloromethane (5 ml) was added. Then, the temperature of the flask was increased to 0° C. After stirring for 2 hours under a nitrogen atmosphere diethyl ether (15 ml) was added, the solution was washed with 1 N aqueous hydrochloric acid (15 ml) and the mixture was allowed to separate by settling into an aqueous and an organic phase. The organic phase was separated, dried over anhydrous magnesium sulphate and subjected to distillation at sub-atmospheric pressure at a temperature below 45° C. to obtain a residue (0.5 g) containing 1R,cis 2,2-dimethyl-3-(2-oxopropyl)cyclopropanecarbaldehyde (yield 50%).

We claim:

1. A compound of the formula (I)

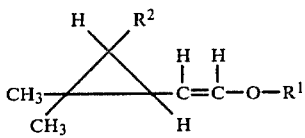 (I)

wherein $R^1$ represents an alkyl group with fewer than six carbon atoms and $R^2$ a 2-oxopropyl group or a 2,2-dihalovinyl group and the compound has the 1R,cis form in which 1 denotes the underlined carbon atom in the group H—$\underline{C}$—C(H)=C in formula I.

2. A compound according to claim 1 wherein $R^1$ represents a methyl group.

3. (1R,cis)-2-[2-(2,2-Dichlorovinyl)-3,3-dimethylcyclopropyl]vinyl methyl ether.

4. (1R,cis)-2-[2,2-Dimethyl-3-(2-oxopropyl)cyclopropyl]vinyl methyl ether.

* * * * *